(12) United States Patent
Yu

(10) Patent No.: US 9,724,239 B2
(45) Date of Patent: Aug. 8, 2017

(54) MOVABLE WIDE-ANGLE OPHTHALMIC SURGICAL SYSTEM

(71) Applicant: NOVARTIS AG, Basel (CH)

(72) Inventor: Lingfeng Yu, Rancho Santa Margarita, CA (US)

(73) Assignee: Novartis AG (CH)

( * ) Notice: Subject to any disclaimer, the term of this patent is extended or adjusted under 35 U.S.C. 154(b) by 149 days.

(21) Appl. No.: 14/331,079

(22) Filed: Jul. 14, 2014

(65) Prior Publication Data

US 2016/0008169 A1   Jan. 14, 2016

(51) Int. Cl.

| A61B 3/14 | (2006.01) |
|---|---|
| A61F 9/009 | (2006.01) |
| A61B 3/10 | (2006.01) |
| A61B 90/50 | (2016.01) |
| G02B 21/00 | (2006.01) |
| A61B 5/00 | (2006.01) |
| A61B 3/117 | (2006.01) |

(Continued)

(52) U.S. Cl.
CPC .............. *A61F 9/009* (2013.01); *A61B 3/102* (2013.01); *A61B 90/50* (2016.02); *A61F 9/00821* (2013.01); *G02B 21/0012* (2013.01); *A61B 3/1176* (2013.01); *A61B 5/0095* (2013.01); *A61B 5/4836* (2013.01); *A61B 90/20* (2016.02); *A61F 2009/00851* (2013.01); *A61F 2009/00874* (2013.01); *A61F 2009/00891* (2013.01); *A61F 2009/00897* (2013.01)

(58) Field of Classification Search
CPC ................... A61F 9/009; A61F 9/008

USPC ............................................. 606/6
See application file for complete search history.

(56) References Cited

U.S. PATENT DOCUMENTS 6,902,326 B1 *  6/2005  Ames ...................... G02B 6/262
                                                                      385/60
8,403,921 B2 *  3/2013  Palankar ............. A61F 9/00736
                                                                      606/2

(Continued)

FOREIGN PATENT DOCUMENTS

| CN | 103251382 A | 8/2013 |
|---|---|---|
| CN | 103314270 A | 9/2013 |

(Continued)

OTHER PUBLICATIONS

International Search Report and Written Opinion issued for PCT/US2014/071153, dated Mar. 31, 2015, 11 pgs.

*Primary Examiner* — Tse Chen
*Assistant Examiner* — Joanne Hoffman

(57) ABSTRACT

A surgical imaging system can include at least one light source, configured to generate a light beam; a beam guidance system, configured to guide the light beam from the light source; a beam scanner, configured to receive the light from the beam guidance system, and to generate a scanned light beam; a beam coupler, configured to redirect the scanned light beam; and a wide field of view (WFOV) lens, configured to guide the redirected scanned light beam into a target region of a procedure eye; wherein the beam coupler is movably positioned relative to the procedure eye such that the beam coupler is selectively movable to change at least one of an incidence angle of the redirected scanned light beam into the procedure eye and the target region of the procedure eye.

19 Claims, 9 Drawing Sheets

(51) Int. Cl.
*A61F 9/008* (2006.01)
*A61B 90/20* (2016.01)

(56) References Cited

U.S. PATENT DOCUMENTS

| | | | |
|---|---|---|---|
| 2008/0212738 A1* | 9/2008 | Gertner | A61N 5/10 378/65 |
| 2009/0257065 A1 | 10/2009 | Hauger et al. | |
| 2010/0324543 A1 | 12/2010 | Kurtz | |
| 2011/0202044 A1 | 8/2011 | Goldshleger et al. | |
| 2012/0092615 A1 | 4/2012 | Izatt et al. | |
| 2012/0274900 A1 | 11/2012 | Horn et al. | |
| 2013/0096543 A1 | 4/2013 | Palanker et al. | |
| 2013/0141695 A1 | 6/2013 | Buckland et al. | |
| 2013/0194581 A1 | 8/2013 | Yoshida | |
| 2013/0231644 A1 | 9/2013 | Hanft et al. | |
| 2013/0235343 A1* | 9/2013 | Hee | A61B 3/102 351/206 |
| 2013/0278898 A1* | 10/2013 | Kato | A61B 3/1005 351/208 |
| 2014/0107634 A1* | 4/2014 | Vogler | A61F 9/008 606/6 |
| 2014/0125952 A1 | 5/2014 | Buckland et al. | |
| 2015/0018645 A1* | 1/2015 | Farkas | A61B 90/96 600/317 |
| 2015/0230702 A1* | 8/2015 | Uhlhorn | A61B 3/14 351/206 |

FOREIGN PATENT DOCUMENTS

| | | |
|---|---|---|
| EP | 2815694 A1 | 12/2014 |
| WO | 2012166116 A1 | 12/2012 |

\* cited by examiner

MOVABLE WIDE-ANGLE OPHTHALMIC SURGICAL SYSTEM

BACKGROUND

Technical Field

Embodiments disclosed herein are related to improved visualization for vitreo-retinal, glaucoma, or other ophthalmic surgeries. More specifically, embodiments described herein relate to a movable wide-angle ophthalmic surgical system that can be implemented as a diagnostic imaging system and/or a treatment beam delivery system.

Related Art

Developing techniques to assist ophthalmic surgery with imaging and visualization is one of the hottest areas of development and innovation. One class of ophthalmic surgeries, the vitreo-retinal procedure, involves vitrectomy, the removal of the vitreous body from the posterior chamber to access the retina. The successful execution of vitrectomy requires an essentially complete removal of the vitreous, including the most challenging regions near the vitreous base. Using imaging techniques and devices can be of substantial help to improve the efficiency of the vitreous removal.

However, assisting vitrectomy with imaging is particularly challenging for several reasons. One of them is that the vitreous is transparent. Another challenge is that visualization of the periphery requires imaging beams with a high angle of obliqueness. Wide angle contact-based or non-contact based lenses are commonly used to address the latter challenge, with only limited success. There are many other reasons that surgeons need to have a wider field of view into the eye in vitreoretinal surgeries, such as for retinal break detection, photocoagulation, etc. Wide-angle contact based lenses can reach approximately 120° field of view, while non-contact based lenses offer an even narrower field of view. Sometimes, surgeons have to rotate the patient's eyeball or perform sclera depression to move the eye into the microscope field of view for observation.

Improvement of the imaging can be achieved by using optical coherence tomography (OCT), a technique that enables visualization of the target tissue in depth by focusing a laser beam onto the target, collecting the reflected beam, interfering the reflected beam with a reference beam and detecting the interference, and measuring the reflectance signature within the depth of focus of the beam. The result is a line scan in depth, a cross-sectional scan, or a volumetric scan.

OCT has become common practice in the clinic as a diagnostic tool. Surgeons take pre-op images into the operating room for reference. OCT scanning is currently not available in the operating room, and thus does not support decision making during surgery. Pre-op images have limited utility following morphologic modifications to the target during a procedure.

Efforts to develop real-time intra-surgical OCT systems are being made by multiple companies ranging from startups to large corporations. The approaches to intra-surgical OCT to date have been microscope-based, handheld probe-based, or endoprobe-based. Microscope-based OCT systems have conventionally mounted the OCT system to the microscope with a fixed orientation with respect to the microscope and/or a patient's eye. Accordingly, integrating OCT into standard surgical microscopes can require substantial modifications of the microscope. Further, even with these modifications, the scanning angle and/or the target location of the OCT beam into the eye is fixed and limited. Moving the patient and/or microscope, both of which can be impractical or infeasible, are the only options for change the scanning angle and/or the target location of the OCT beam.

SUMMARY

The presented solution fills an unmet medical need with a unique solution to provide movable wide-angle diagnostic imaging and/or treatment beam delivery system intra-surgically, without surgical overhead or disruption to the surgical workflow, with an adjustable beam scanning/delivery angle and/or location in the eye to maximize usability.

Consistent with some embodiments, an ophthalmic surgical system comprises: at least one light source, configured to generate a light beam; a beam guidance system, configured to guide the light beam from the at least one light source; a beam scanner, configured to receive the light from the beam guidance system, and to generate a scanned light beam; a beam coupler, configured to redirect the scanned light beam; and a wide field of view (WFOV) lens, configured to guide the redirected scanned light beam into a target region of a procedure eye; wherein the beam coupler is movably positioned relative to the procedure eye such that the beam coupler is selectively movable to change at least one of an incidence angle of the redirected scanned light beam into the procedure eye and the target region of the procedure eye.

Consistent with some embodiments, a method of operating a surgical optical coherence tomography (OCT) visualization comprises: generating an imaging light beam using a light source; guiding the imaging light beam from the light source to a beam scanner using a beam guidance system; generating a scanned imaging light beam using the beam scanner; redirecting the scanned imaging light beam using a beam coupler, including redirecting the scanned imaging light beam into the optical pathway of a surgical microscope; guiding the redirected scanned imaging light beam into a target region of a procedure eye using a wide field of view (WFOV) lens; and selectively moving the beam coupler to change at least one of an incidence angle of the redirected scanned imaging light beam into the procedure eye and the target location of the procedure eye.

Additional aspects, features, and advantages of the present disclosure will become apparent from the following detailed description.

Figure 1:
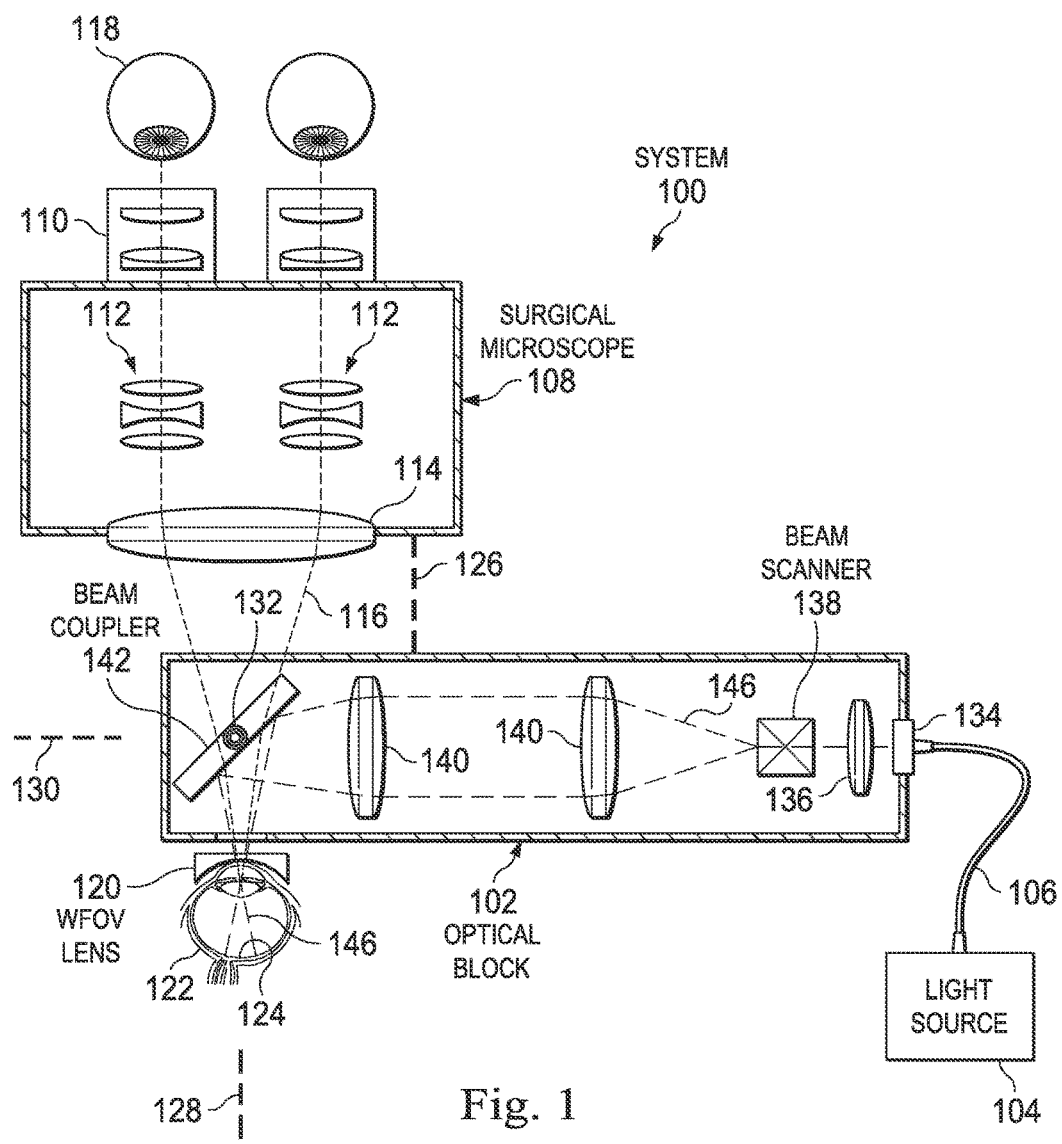
FIG. 1 is a diagram illustrating a movable wide-angle ophthalmic surgical system.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

The real-time, intra-surgical, adjustable wide-field of view imaging systems of the present disclosure provide numerous advantages relative to microscope-based OCT systems, including (1) reduced complexity of usage with a large number of different surgical microscopes; (2) optical access to large variety of laser scanning visualization techniques; and (3) wider scan angles, including the ability to scan in the periphery of the eye, by permitting rotational and translation motion that changes the incidence angle and/or incidence location of the scanning beam in the eye. The real-time, intra-surgical, adjustable wide-field of view imaging systems of the present disclosure also provide numerous advantages relative to handheld probe-based OCT systems, including (1) hands-free imaging; (2) simplified surgical workflow; (3) more stabilized OCT imaging with fewer motion related artifacts; and (4) simultaneous OCT imaging and microscope observation. The real-time, intra-surgical, adjustable wide-field of view imaging systems of the present disclosure also provide numerous advantages relative to endoprobe-based OCT systems, including (1) non-invasive OCT imaging; (2) simplified surgical workflow; (3) volume scan ability; (4) more stabilized OCT imaging with fewer motion related artifacts; (5) improved lateral resolution; and (6) the ability to be combined with surgical microscope imaging. Many similar advantages can be realized using the real-time, intra-surgical, adjustable wide-angle treatment beam delivery systems of the present disclosure.

The ophthalmic surgical system of the present disclosure can be configured to facilitate delivery of intra-surgical, adjustable wide angle laser scanning via a movable beam coupler. The beam coupler, together with one or more optical elements, can be part of an integrated optical block component. The entirety of the optical block can be rotated or translated, or the beam coupler can be rotated independent of the optical block. A wide-field of view for laser scanning can be provided as selective movement of the beam coupler changes the angle of incidence of the scanning beam into the eye and/or the incidence location of the scanning beam in the eye. The movable wide-angle ophthalmic surgical system can be implemented as diagnostic imaging system(s) such as optical coherence tomography (OCT), multispectral imaging, fluorescence imaging, photo-acoustic imaging, etc., as well as treatment beam delivery system(s) for laser treatment such as photocoagulation. The wide-angle laser scanning can be diagnostic and/or therapeutic in nature. Diagnostic laser scanning can include optical coherence tomography (OCT) imaging. For example, such a system may provide adjustable, wide-field intra-surgical OCT without disrupting the surgical workflow. The treatment laser scanning can include laser beam scanning. The scanning beam can be delivered into the eye through a contact based or non-contact based surgical lens. If non-visible laser wavelengths are used, then the contact lens can also serve as a standard surgical contact lens. A non-contact WFOV lens can be implemented in a manner similar to a binocular indirect ophthalmomicroscope (BIOM). Coupled with a real-time acquisition and display system, the diagnostic imaging and/or treatment beam delivery system can improve intra-surgical visualization. Further, the diagnostic imaging and/or treatment beam delivery system can be operable independent of a microscope, and can even be used without a microscope. The diagnostic imaging and/or treatment beam delivery system can also be coupled to a stereoscopic camera viewing system as a microscope replacement technology and/or a surgical guidance technology for surgical robots or remote surgical systems.

FIG. 1 illustrates a diagnostic imaging and/or treatment beam delivery system 100. The diagnostic imaging and/or treatment beam delivery system 100 can include at least one light source 104 configured to generate a diagnostic and/or treatment light beam. For example, in some embodiments, diagnostic imaging and/or treatment beam delivery system 100 can include one light source to generate the diagnostic light beam and one light source to generate the treatment light beam. In some embodiments, the light source 104 can be configured to generate both the diagnostic light beam and the treatment light beam. The light source 104 can be part of a diagnostic imaging system, such as an OCT imaging system, a multispectral imaging system, a fluorescence imaging system, a photo-acoustic imaging system, etc. For example, the light beam can be part of an OCT scanning beam. The light source 104 can have an operating wavelength in the 0.2-1.8 micron range, the 0.7-1.4 micron range, and/or the 0.9-1.1 micron range. The light source 104 can be part of a treatment beam delivery system, such as a laser beam delivery system. The diagnostic imaging system and/or the treatment beam delivery system can include one or more additional components (e.g., a beam guidance system, a beam scanner, etc.).

The diagnostic imaging and/or treatment beam delivery system 100 can include a beam guidance system, including an optical fiber 106 and/or free space, configured to guide the light beam from the light source 104. The diagnostic imaging and/or treatment beam delivery system can include a collimator 136 that is configured to receive the light beam from the beam guidance system and collimate light.

The diagnostic imaging and/or treatment beam delivery system 100 can include an optical beam scanner 138 configured to receive the light beam from the collimator 136 and/or the beam guidance system, and generate a scanned light beam 146. For example, the beam scanner 138 can be configured to receive the diagnostic light beam from the beam guidance system and to generate a scanned diagnostic light beam. The beam scanner 138 can be configured instead or additionally to receive the treatment light beam from the beam guidance system and generate a scanned treatment light beam. The beam scanner 138 can be configured to generate the scanned light beam 146 having any desired one-dimensional or two-dimensional scan patterns, including a line, a spiral, a raster, a circular, a cross, a constant-radius asterisk, a multiple-radius asterisk, a multiply folded path, and/or other scan patterns. The beam scanner 138 can include one or more of a pair of scanning mirrors, a micro-mirror device, a MEMS based device, a deformable platform, a galvanometer-based scanner, a polygon scanner, and/or a resonant PZT scanner.

The diagnostic imaging and/or treatment beam delivery system 100 can also include a beam coupler 142 configured to redirect the scanned light beam 146 towards a wide field of view (WFOV) lens 120 configured to guide the redirected scanned light beam into a target region 124 of a procedure eye 122. The target region 124 can include the retina, macula/fovea, optic disk, vitreous body, and/or trabecular meshwork/Schlemm's canal. The diagnostic imaging and/or treatment beam delivery system 100 can be configured to image these and other particular regions-of-interest with higher resolution.

Figure 7:
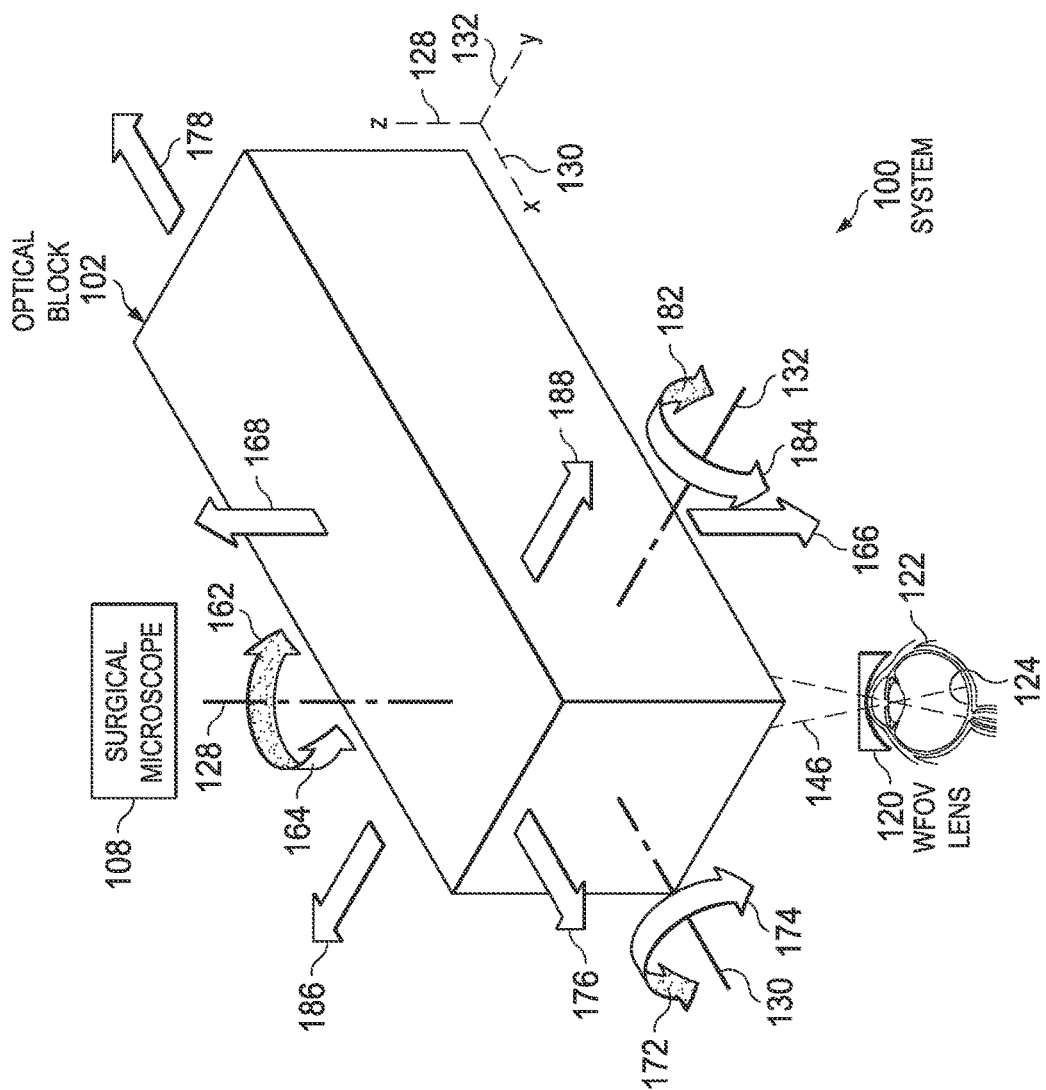
FIG. 7 is a diagram illustrating a movable wide-angle ophthalmic surgical system.

The diagnostic imaging and/or treatment beam delivery system 100 can also include a surgical microscope 108 (FIGS. 1 and 7). An observer 118 can view the procedure eye 122 through the eyepiece 110 of the surgical microscope 108. An optical pathway 116 of the surgical microscope 108 can include one or more focusing/zoom lenses of the eyepiece 110, one or more focusing/zoom lenses 112 of the microscope body, and an objective lens 114.

The beam coupler 142 can be configured to redirect the scanned light beam 146 into the optical pathway 116 of the surgical microscope 108. To redirect the scanned light beam 146 into the target region 124 of the procedure eye 122 and/or the optical pathway 116 of the surgical microscope, the beam coupler 142 can include a mirror. As shown in FIGS. 1-6 and 8a-9b, the mirror can be tilted such that it is oriented at an oblique angle with respect to each of the scanned light beam 146 and the optical pathway 116 of the surgical microscope 108. The beam coupler 142 can include a dichroic mirror, a notch filter, a hot mirror, a beamsplitter and/or a cold mirror. The beam coupler 142 can be configured to combine the visible beam of the microscope 108 with the scanned light beam 146. As a result, the field of view of the scanned light beam 146 and the microscope 108 can overlap completely, overlap partially, or not overlap at all. The beam coupler 142 can be configured to reflect the scanned light beam 146 and/or reflections from the procedure eye 122 in the wavelength range of the scanned light beam 142 while allowing the visible beam of the microscope 108 to pass therethrough.

The beam scanner 138 and/or the optical block 102 can also include focusing optics for defining a depth of focus of the scanned light beam 146. For example, one or more lenses 140 can be included within the optical block 102 (FIGS. 1-6 and 8a-9b). When present, the focusing optics of the beam scanner 138 and/or the optical block 102 can be fixed or adjustable. Focusing optics or zoom lenses within the beam scanner 138 and/or optical block 102 can facilitate scanning of a region of interest with increased resolution and depth-of-field. The focusing optics and/or zoom lenses can be provided at one or more of the following locations: between the beam coupler 142 and the surgical microscope 108; between the beam coupler 142 and the WFOV lens 120; between the beam coupler 142 and the beam scanner 138; and between the beam scanner 138 and the light source 104. Focusing optics and/or zoom lenses positioned between the beam coupler 142 and the surgical microscope 108 can be configured to adjust the focus of the optical pathway 116 of the surgical microscope 108. Focusing optics and/or zoom lenses positioned between the beam coupler 142 and the beam scanner 138 or between the beam scanner 138 and the light source 104 can be configured to adjust the focus of the scanned light beam 146. Focusing optics and/or zoom lenses positioned between the beam coupler 142 and the WFOV lens 120 can be configured to adjust the focus of both the optical pathway 116 of the surgical microscope 108 and the scanned light beam 146.

The lens(es) 140 can be adjusted by a zoom-controller to adapt an optical power of the diagnostic imaging and/or treatment beam delivery system 100 to the desired target region 124 of the procedure eye 122. Further, the adjustable zoom lens(es) 140 can be controlled by the zoom-controller in real-time to adapt the optical power of the diagnostic imaging and/or treatment beam delivery system 100 to keep an aberration below a predetermined value as the scanned light beam 146 scans across the target region 124 of the procedure eye 122. In that regard, the zoom-controller can control each adjustable zoom lens 140 by adjusting a physical position of the zoom lens 140 (e.g., using piezo-electric or other suitable actuators) and/or adjusting an optical power of the zoom lens 140 without adjusting the physical position of the zoom lens 140 (e.g., by varying a voltage supplied to a liquid crystal zoom lens).

Figure 2:
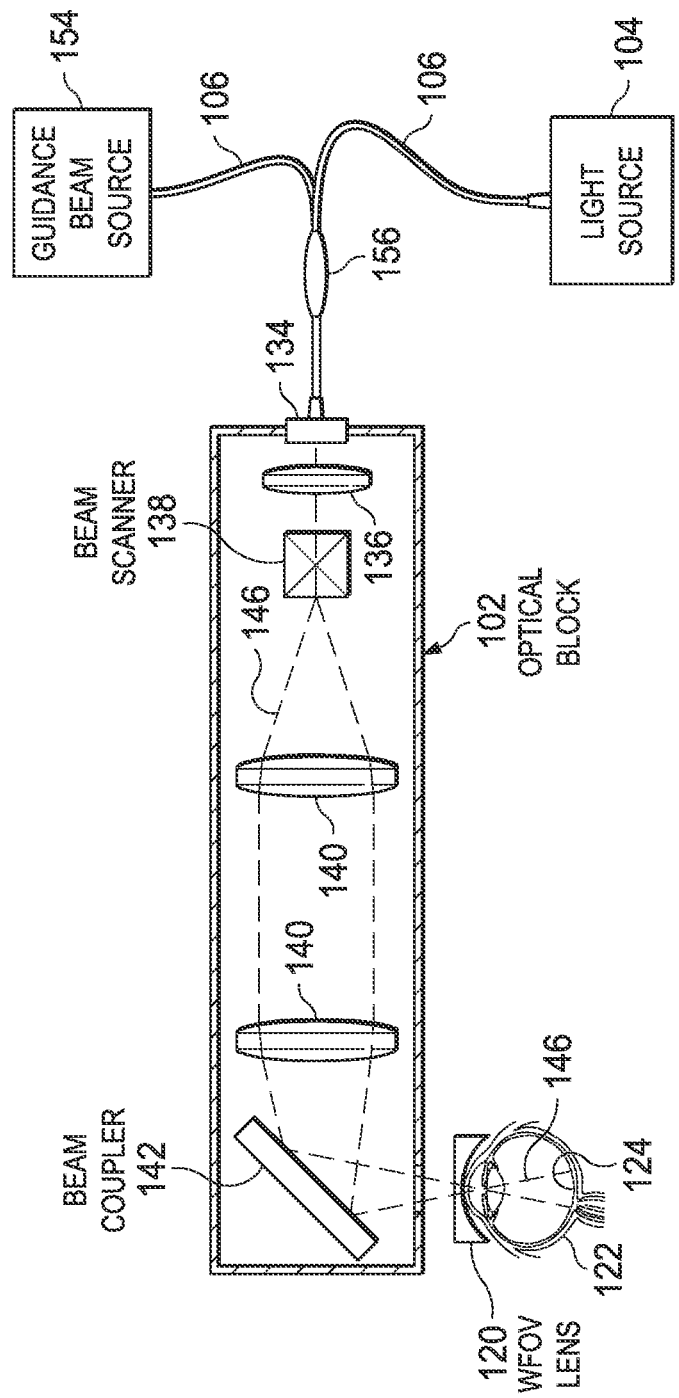
FIG. 2 is a diagram illustrating a movable wide-angle ophthalmic surgical system.

In some embodiments, the diagnostic imaging and/or treatment beam delivery system 100 can include a visible guidance beam, such as when the scanned light beam 146 is outside of the visible range. For example, the scanned light beam 146 can be in the infrared range. As shown in FIG. 2, the diagnostic imaging and/or treatment beam delivery system 100 can include a guidance beam source 154 configured to generate the visible guidance beam. The visible guidance beam, via an optical fiber 106, can be coupled into the surgical imaging and/or beam delivery system 100 using a coupler, wavelength division multiplexer (WDM), or beam splitter 156. The coupler, WDM, or beam splitter 156 can be positioned before the beam scanner 138. The beam coupler 142 can be configured to reflect at least a portion of a visible guidance beam coincident with the scanned light beam 146 to facilitate visualization of the scanned light beam 146. For example, the beam coupler 142 can include a notch filter in the wavelength range of the visible guidance beam such that the visible guidance beam can be reflected by beam coupler 142 along with the scanned light beam 146 to reach the procedure eye 122.

Referring again to FIG. 1, in some embodiments, the diagnostic imaging and/or treatment beam delivery system 100 can include an integrated optical block component 102. The optical block 102 can include one or more optical elements integrated into a common component, such as a hand-held device, a lens holder, an adapter, or other component. The optical block 102 can be a consumable product configured for use in a single surgical procedure or reusable in multiple surgical procedures. The optical block 102 can be independently positionable relative to the surgical microscope 108 and/or the procedure eye 122. FIGS. 1-7 and 8a-9b illustrate various embodiments of the optical block 102. For example, the optical block 102 can include the optical beam scanner 138, the beam coupler 142, one or more lenses 140, the collimator 136, etc. In various embodiments, the optical block 102 can include more or fewer components. The optical block 102 can be in optical communication with the light source 104 via the optical fiber 106. The optical block 102 can include a fiber holder 134 where the optical fiber 106 is mechanically received in the optical block 102.

Figure 3:
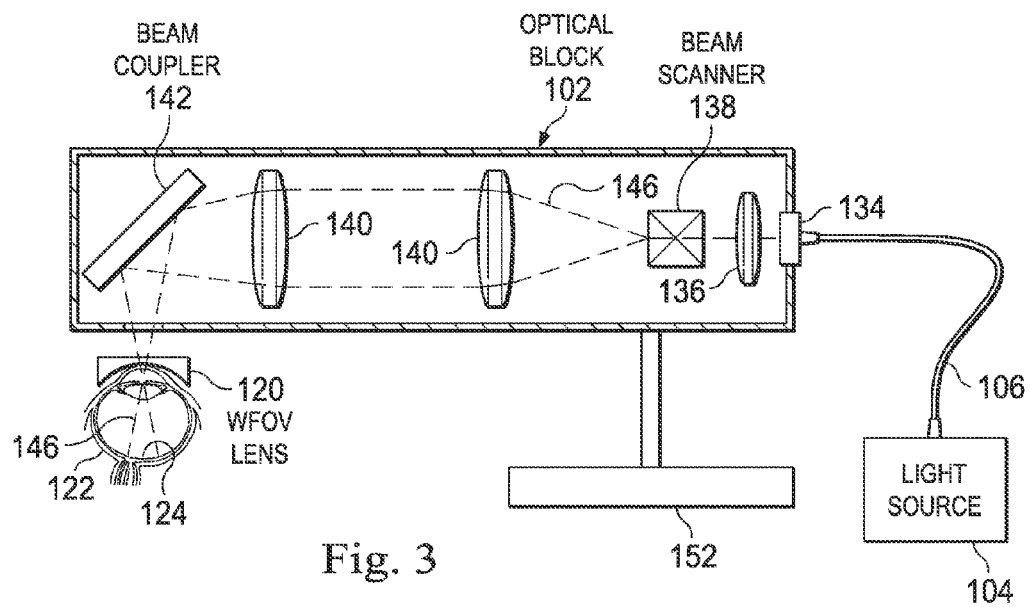
FIG. 3 is a diagram illustrating a movable wide-angle ophthalmic surgical system.

The beam coupler 142 and/or the optical block 102 can be operated with or without a defined optical/optomechanical relationship to the surgical microscope 108. For example, the beam coupler 142 or the optical block 102 can be maintained separate from and independently positionable relative to the surgical microscope 108. In such instances, the beam coupler 142 can be a hand-held device, a lens holder, a self-stabilized component or other component. As shown in FIG. 3, the optical block 102 can be coupled to a support arm 152. The support arm 152 can be stationary, such as when the support arm 152 is wall-mounted. The support arm 152 can be movable, such as when the support arm 152 is mounted on a movable pole or cart. As described with respect to FIGS. 7-9*b*, the optical block 102 can be coupled to the support arm 152 such that optical block 102 is movable with six degrees of freedom (e.g., three rotational degrees of freedom and three translation degrees of freedom) relative to the surgical microscope 108 and/or the procedure eye 122.

Referring again to FIG. 1, the beam coupler 142 and/or the optical block 102 can be coupled to the surgical microscope 108, directly or indirectly, such that it has a defined optical/optomechanical relationship to the surgical microscope. For example, direct or indirect coupling 126 between the optical block 102 and the surgical microscope 108 can include one or more of a suspension system, a mechanical frame, a protruding arm, a conical structure, a magnetic member, an elastic member, and a plastic member. The WFOV lens 120 can be independently manipulable relative to the procedure eye 122 by a lens-holder—instead of the beam coupler 142—when the beam coupler 142 is coupled to the surgical microscope in a defined optical/optomechanical relationship. As described with respect to FIGS. 7-9*b*, the optical block 102 can be coupled to the surgical microscope 108 such that the optical block 102 is movable with six degrees of freedom (e.g., three rotational degrees of freedom and three translation degrees of freedom) relative to the surgical microscope 108 and/or the procedure eye 122.

Referring again to FIG. 1, the WFOV lens 120 of the diagnostic imaging and/or treatment beam delivery system 100 can be configured to provide a field of view of the procedure eye 122 greater than 15 degrees, greater than 30 degrees, greater than 45 degrees, greater than 60 degrees, greater than 80 degrees and/or greater than 100 degrees. Accordingly, the diagnostic imaging and/or treatment beam delivery system 100 can be configured to provide various field of view ranges, such as between 0 degrees and 30 degrees, between 15 degrees and 80 degrees, between 30 degrees and 120 degrees, and/or other desired ranges up to ora serrata within the field of view of the WFOV lens 120. The WFOV lens 120 can be configured to provide the desired refractive power for the diagnostic and/or treatment procedures to be performed on the procedure eye 122.

Figure 4:
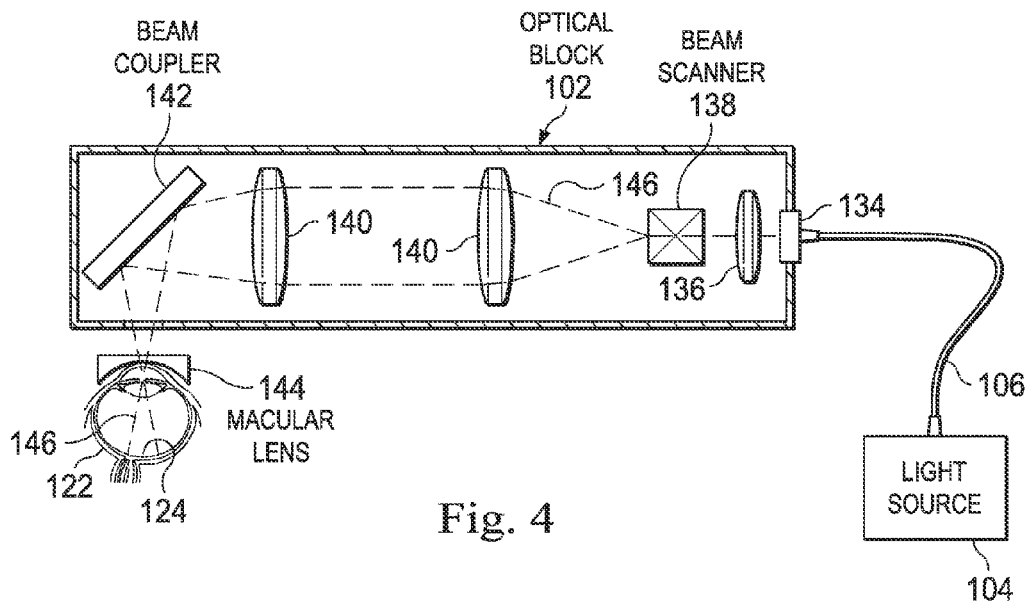
FIG. 4 is a diagram illustrating a movable wide-angle ophthalmic surgical system.

The WFOV lens 120 can be configured to operate in contact with the procedure eye 122, as a contact lens, or spaced from the procedure eye 122, as a non-contact lens. As shown in FIG. 4, the contact lens can be a macular lens 144 configured to be contacted to the procedure eye 122. A macular lens 144 can be embedded in a stabilizing mechanism, where the stabilizing mechanism can be configured to stabilize the macular lens 144 relative to the procedure eye 122. To that end, the stabilizing mechanism can include one or more of a trocar, a counter weight, a friction-based system, and an elastic system. In some embodiments, the WFOV lens 120 can be separate from, but attachable to the optical block 102.

Figure 5:
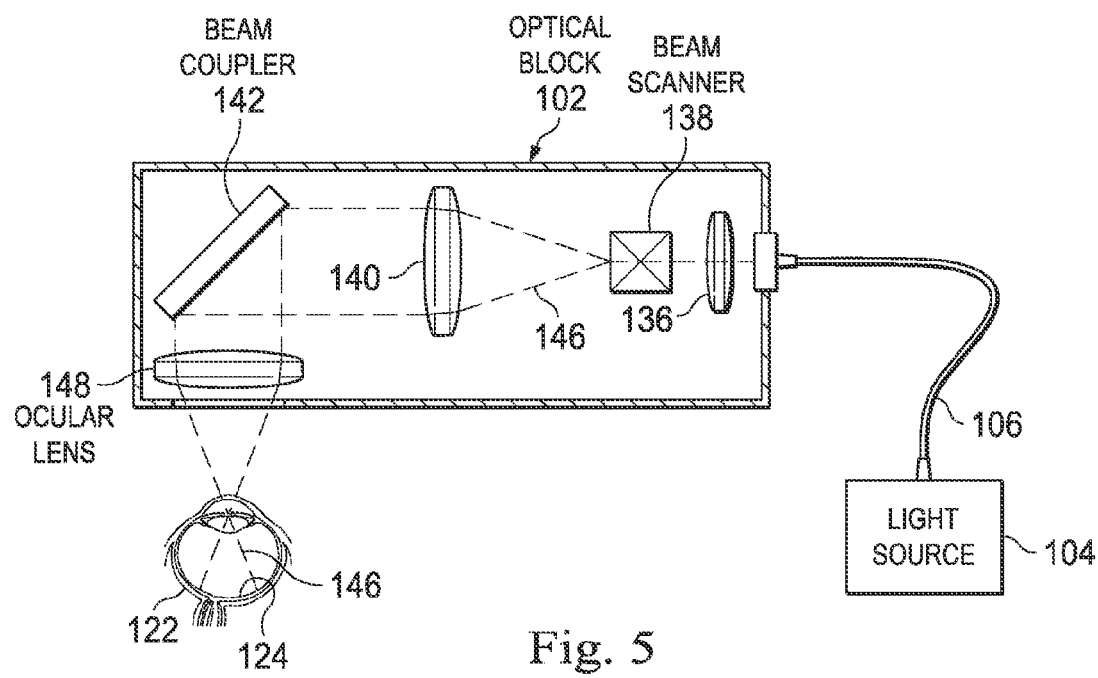
FIG. 5 is a diagram illustrating a movable wide-angle ophthalmic surgical system.
Figure 6:
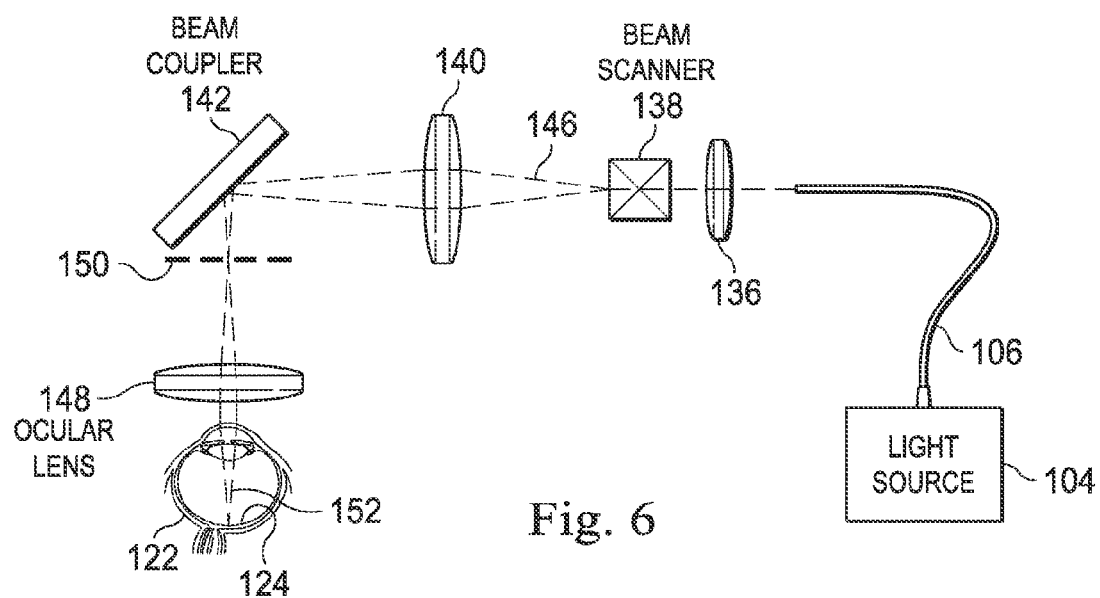
FIG. 6 is a diagram illustrating a movable wide-angle ophthalmic surgical system.

As shown in FIGS. 5 and 6, the non-contact WFOV lens can be an ocular lens 148 that is spaced from the procedure eye 122. An intermediate image plane 150 between the beam coupler 142 and the ocular lens 148 can be generated in embodiments of the diagnostic imaging and/or treatment beam delivery system 100 including the ocular lens 148. The ocular lens 148 can be configured to operate in a manner similar to a binocular indirect ophthalmomicroscope (BIOM). The ocular lens 142 can be positioned by one or more of a mechanical coupling to the beam coupler 142, the optical block 102, a mechanical coupling to the surgical microscope 108, a suspension system, and a lens holder. In some embodiments, the WFOV lens 120 can be one optical element of the optical block 102. The optical block 102, the beam coupler 142, and/or the ocular lens 148 can be moved as described with respect to FIGS. 7-9*b* to change the incidence angle and/or the target location of the scanned light beam 146 in the procedure eye 122.

The light source 104, the beam guidance system, and the beam scanner 138 can be part of an optical coherence tomographic (OCT) imaging system. To that end, the WFOV lens 120 and the beam coupler 142 can be configured to guide a returned image light from the target region 124 of the procedure eye 122 back to the OCT imaging system. The returned image light can be interfered with a reference beam of the OCT imaging system, and from the interference an OCT image of the target region in a range of depths can be generated and displayed to a user. The diagnostic imaging and/or treatment beam delivery system can be configured to generate the imaging information based on processing the returned image light in less than 30 seconds, less than 10 seconds, and/or less than 5 seconds, including in real time. A single scanned light beam 152 or A-scan is shown in FIG. 6. The single scanned light beam 152 can be focused at a particular location along the target region 124 within the procedure eye 122. Multiple A-scans can be performed within the target region 124 to generate the larger field of view illustrated FIGS. 1-5 and 8*a*-9*b*. As described with respect to FIGS. 7-9*b*, the optical block 102, the beam coupler 142, and/or the WFOV lens 120 can be selectively moved such that the diagnostic imaging and/or treatment beam delivery system 100 has an adjustable field of view. The returned image light from individual A-scans with different incidence angles and/or incidence locations can be processed and combined to generate combined imaging formation (e.g., cross-sectional and/or volumetric OCT data).

FIG. 7 illustrates the diagnostic imaging and/or treatment beam delivery system 100, including rotational and/or translational motion of the optical block 102. The beam coupler 142 and/or the optical block 102 can be movable such that the diagnostic imaging and/or treatment beam delivery system 100 has an adjustable, wide angle scanning. For example, the field of view of the scanned light beam 146 can cover a changeable region of the procedure eye 122. The wide angle scanning or field of view can be adjusted as the incidence angle and/or incidence location of the scanned light beam 146 within the procedure eye 122 changes based on translation and/or rotation of the beam coupler 142 and/or the optical block 102 relative to the surgical microscope 108 and/or the procedure eye 122. In some embodiments, movement of the optical block 102 includes movement of the beam coupler 142. In some embodiments, movement of the beam coupler 142 is independent of movement of the optical block 102. In embodiments of the diagnostic imaging and/or treatment beam delivery system 100 including a non-contact WFOV lens, the ocular lens 148 (FIGS. 5 and 6) can be moved along with the beam coupler 142 and/or the optical block 102. The beam coupler 142 and/or the optical block 102 can be selectively moved to scan in the periphery of the procedure eye 122. The beam coupler 142 and/or the optical block 102 can be selectively moved to scan the trabecular meshwork or Schlemm's canal of the procedure eye 122. Further, the beam coupler 142 and/or the optical block 102 can be positioned such that the field of view of the scanned light beam 146 and the field of view of the visible beam of the microscope do not overlap, partially or entirely overlap.

Selective movement of the beam coupler 142 and/or the optical block 102 can be configured to provide a field of view of the procedure eye 122 greater than 15 degrees, greater than 30 degrees, greater than 45 degrees, greater than 60 degrees, greater than 80 degrees and/or greater than 100 degrees. Accordingly, the diagnostic imaging and/or treatment beam delivery system 100 can be configured to provide various field of view ranges, such as between 0 degrees and 30 degrees, between 15 degrees and 80 degrees, between 30 degrees and 120 degrees, and/or other desired ranges up to ora *serrata*.

In some embodiments, the optical block 102 can be movable with one, two, three, four, five, six, or more degrees of freedom. For example, the optical block 102 can have one, two, three, or more rotational degrees of freedom. A first rotational degree of freedom can be about an axis 128 or z-axis (FIGS. 1 and 7). As shown in FIG. 1, the optical block 102 can rotate about the axis 128 into and out of the plane of the page. The axis 128 can be central axis of the surgical microscope 108. As shown in FIG. 7, the optical block 102 can rotate in directions 162 and 164 about the axis 128. By itself, rotation about the axis 128 does not change the incidence angle and/or the incidence location of the scanned light beam 146 in the procedure eye 122. However, rotation about the axis 128 provides flexibility to the observer 118, such as a surgeon, to move the optical block 102 to a more convenient orientation during the surgical procedure. For example, the observer 118 can rotate the optical block 102 based on the how the patient is positioned, which eye is being operated on, etc.

Figure 8A:
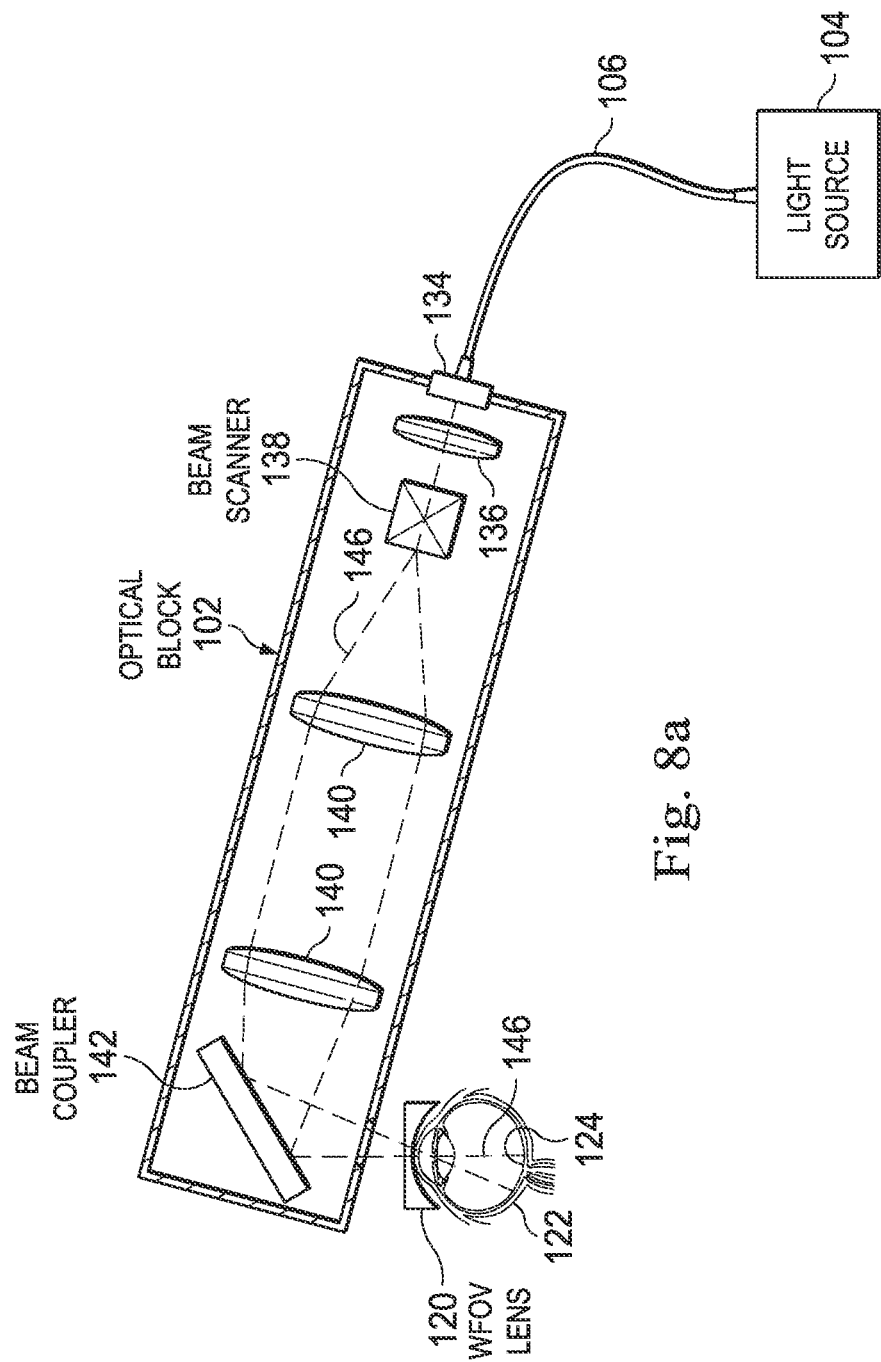
FIG. 8a is a diagram illustrating a movable wide-angle ophthalmic surgical system.
Figure 8B:
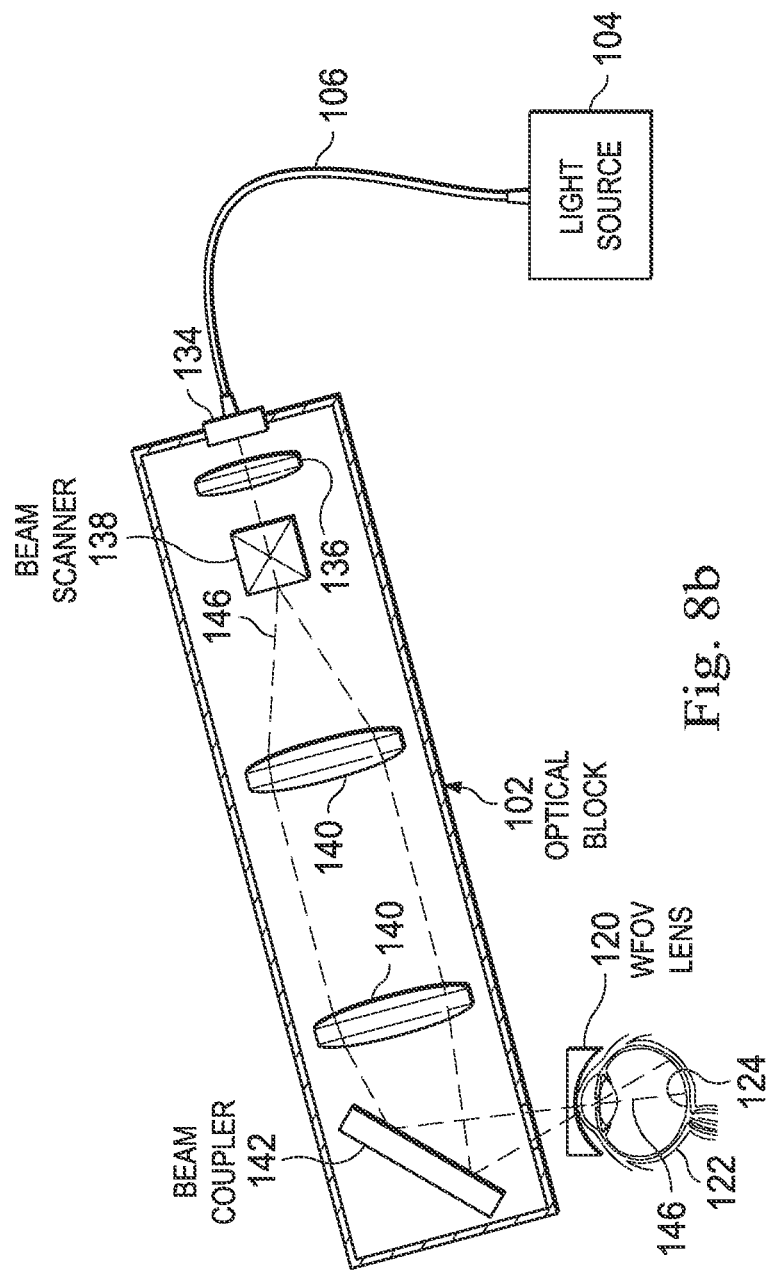
FIG. 8b is a diagram illustrating a movable wide-angle ophthalmic surgical system.

A second rotational degree of freedom can be about an axis 132 or y-axis (FIGS. 1 and 7). Rotation about the axis 132 can be described as tilting the optical block 102. As shown in FIG. 1, the axis 132 extends into and out of the page, and the optical block 102 can rotate about the axis 132 in the plane of the page. As shown in FIG. 7, the optical block 102 can rotate in directions 182 and 184 about the axis 132. While the axis 132 is shown as extending through the beam coupler 142, the axis can be positioned anywhere along the optical block 102 such that the axis is parallel to the axis 132 shown in FIGS. 1 and 7. Rotation about the axis 132 can change the incidence angle and/or the incidence location of the scanned light beam 146 in the procedure eye 122. Depending on how the patient is positioned relative to the optical block 102, rotation about the axis 132 can shift the scanned light beam 142 to the left, to the right, up, or down in the procedure eye 122. As shown in FIG. 8a, the optical block 102 can be rotated in the direction 182 about the axis 132. As a result, the scanned light beam 146 can be shifted to the left of the target region 124. As shown in FIG. 8b, the optical block 102 can be rotated in the direction 184 about the axis 132. As a result, the scanned light beam 146 can be shifted to the right of the target region 124.

A third rotational degree of freedom can be about an axis 130 or x-axis (FIGS. 1 and 7). As shown in FIG. 7, the optical block 102 can rotate in directions 172 and 174 about the axis 132. Rotation about the axis 130 can change the incidence angle and/or the incidence location of the scanned light beam 146 in the procedure eye 122. Depending on how the patient is positioned relative to the optical block 102, rotation about the axis 130 can shift the scanned light beam 142 to the left, to the right, higher, or lower in the procedure eye 122. For example, rotation in the direction 172 can shift the scanned light beam 146 to the right in procedure eye. Rotation in the direction 174 can shift the scanned light beam 146 to the left in the procedure eye.

For example, the optical block 102 can have one, two, three, more translational degrees of freedom. A first translational degree of freedom can be along the axis 128. As shown in FIG. 1, the optical block 102 can translate along the axis 128 in the plane of the page. As shown in FIG. 7, the optical block 102 can translated in the directions 166 and 168, along the axis 128. Translation along the axis 128 can adjust a focusing depth of the scanned light beam 146 on the target region 124 of the procedure eye 122.

A second translational degree of freedom can be along the axis 132. As shown in FIG. 1, the optical block 102 can translate along axis 132 into and out of the page. As shown in FIG. 7, the optical block 102 can be translated in the directions 186 and 188, along the axis 132. Translation along the axis 132 can change the incidence angle and/or the incidence location of the scanned light beam 146 in the procedure eye 122. Depending on how the patient is positioned relative to the optical block 102, translation along the axis 132 can shift the scanned light beam 146 to the left, to the right, higher, or lower in the procedure eye 122. For example, translation in the direction 186 can shift the scanned light beam 146 to the left in the procedure eye 122. Translation in the direction 188 can shift the scanned light beam 146 to the right in the procedure eye 122.

A third translational degree of freedom can be along the axis 130. As shown in FIG. 1, the optical block 102 can translate along axis 130 in the plane of the page. As shown in FIG. 7, the optical block 102 can be translated in the directions 176 and 178, along the axis 130. Translation along the axis 130 can change the incidence angle and/or the incidence location of the scanned light beam 146 in the procedure eye 122. Depending on how the patient is positioned relative to the optical block 102, translation along the axis 130 can shift the scanned light beam 142 to the left, to the right, higher, or lower in the procedure eye 122. For example, translation in the direction 176 can shift the scanned light beam 146 to the left of the target region 124. Translation in the direction 178 can shift the scanned light beam 146 to the right of the target region 124.

In some embodiments, movement of the optical block 102 can include only rotation or only translation. In some embodiments, movement of the optical block 102 can include both rotation and translation. The optical block 102 can be rotated about and/or translated along one or more of the axes 128, 130, and 132 to provide an adjustable wide field of view for the diagnostic imaging and/or treatment beam delivery system 100. The optical block 102 can be translated in one or more directions and then rotated in one or more directions, or vice versa, in order to direct the scanned light beam 146 into the target region 124 (and prevent the scanned light beam 146 from encountering interference with, e.g., the iris). For example, the optical block 102 can be moved based on the visible guidance beam (FIG. 2) to scan desired locations of the target region 124. Rotation and/or translation of the optical block 102 can be achieved manually (e.g., by physical manipulation by the surgeon) or automatically (e.g., by one or more motorized actuators controlled by a controller of the surgical imaging and/or beam delivery system 100). A contact WFOV lens (e.g., macular lens 144) can maintain a fixed orientation relative to the procedure eye 114 during translation and/or rotation of the optical block 102. A non-contact WFOV lens (e.g., ocular lens 148) can translate and/or rotate along with optical block 102.

Figure 9A:
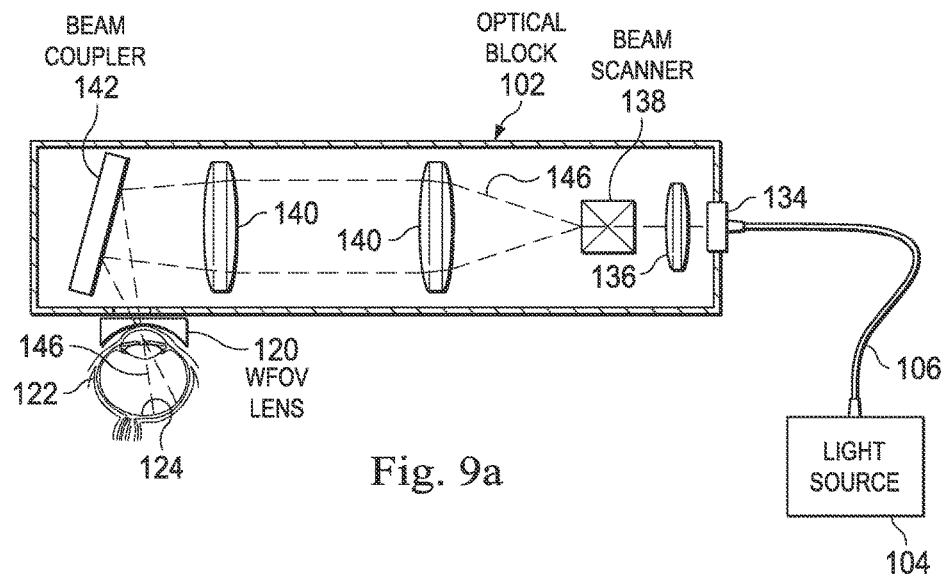
FIG. 9a is a diagram illustrating a movable wide-angle ophthalmic surgical system.
Figure 9B:
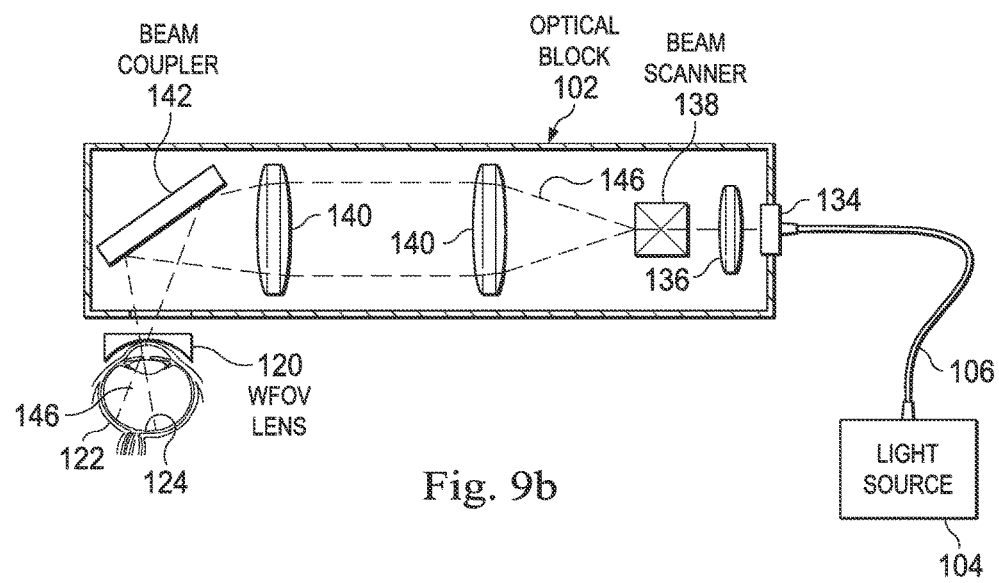
FIG. 9b is a diagram illustrating a movable wide-angle ophthalmic surgical system.

In some embodiments, the beam coupler 142 can be rotatable relative to the procedure eye 122 and/or the microscope 108. Rotation of the beam coupler 142 can be independent of movement of the optical block 102. In that regard, rotation of the beam coupler 142 can be utilized to facilitate full circumferential scanning of the procedure eye 122 and/or to target a particular region of interest within the procedure eye 122. The beam coupler 142 can be rotatable about the axis 132 (FIGS. 1 and 7) or an axis parallel to the axis 132. As shown in FIG. 9a, rotation of the beam coupler 142 in the direction 182 can shift the scanned light beam 146 to the left of the target region 124. As shown in FIG. 9b, rotation of the beam coupler 142 in the direction 184 can shift the scanned light beam 146 to the right of the target region 124. Rotation of the beam coupler 142 can be achieved manually (e.g., by physical manipulation by the surgeon) or automatically (e.g., by one or more motorized actuators controlled by a controller of the diagnostic imaging and/or treatment beam delivery system 100). A contact WFOV lens (e.g., macular lens 144) can maintain a fixed orientation relative to the procedure eye 122 during translation and/or rotation of the beam coupler 142. A non-contact WFOV lens (e.g., ocular lens 148) can translate and/or rotate along with the beam coupler 142.

Figure 10:
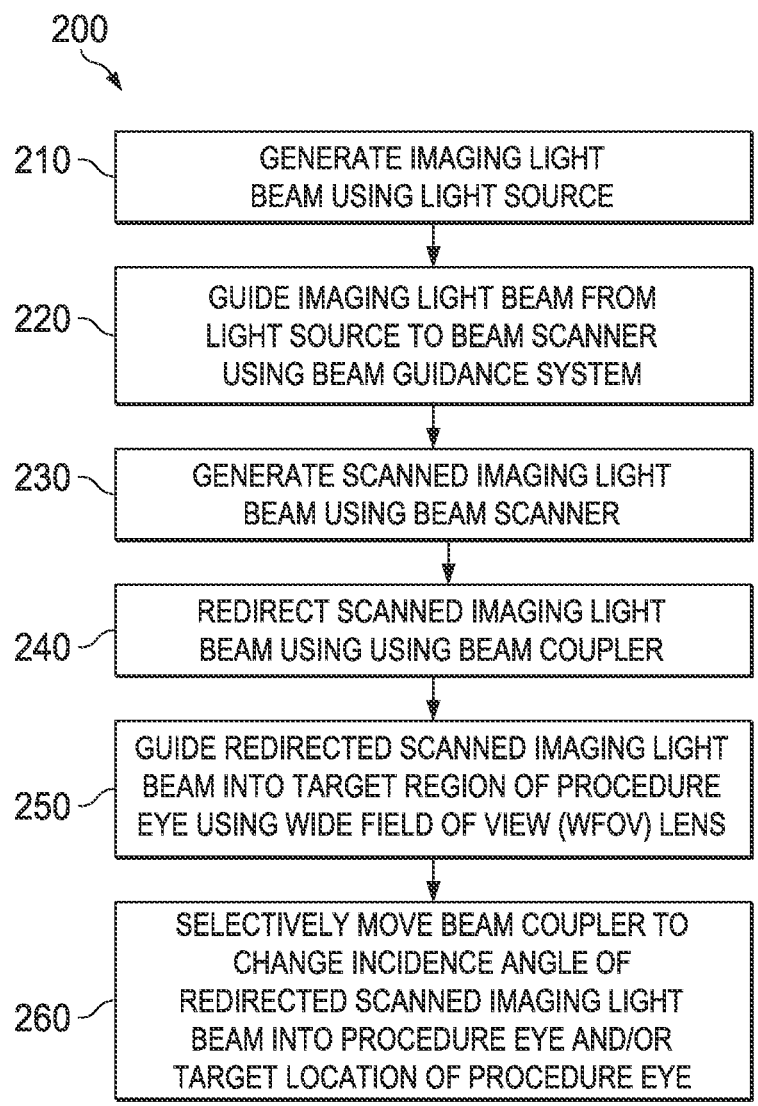
FIG. 10 is a flow diagram illustrating a method of operating a surgical visualization system.

FIG. 10 illustrates a method 200 of operating a wide-angle ophthalmic surgical system, such as a diagnostic imaging system and/or a treatment beam delivery system. The diagnostic imaging system can be, for example, an optical coherence tomography (OCT) visualization system. The method 200 can be further understood with reference to FIGS. 1-9b. The method 200, at step 210, can include generating a diagnostic and/or treatment light beam using a light source. For example, the light beam can be generated using the light source 104. The method 200, at step 220, can include guiding the light beam from the light source to a beam scanner using a beam guidance system. The example, the beam guidance system can include the optical fiber 106 to guide the light beam from the light source 104 to the beam scanner 138. The method 200, at step 230, can include generating a scanned light beam using the beam scanner. For example, the scanned light beam 146 can be generated using the beam scanner 138. The method 200, at step 240, can include redirecting the scanned light beam using a beam coupler. Redirecting the scanned light beam can include redirecting the scanned light beam into an optical pathway of a surgical microscope. For example, the scanned light beam 146 can be redirected using the beam coupler 142. The beam coupler 142 can redirect the scanned light beam 146 into the optical pathway 116 of the microscope 108. The method 200, at step 250, can include guiding the redirected scanned light beam into a target region of a procedure eye using a wide field of view (WFOV) lens. For example, the WFOV lens 120 can be used to guide the scanned light beam 146 into the target region 124 of the procedure eye 122. The method 200, at step 260, can include selectively moving the beam coupler and/or the optical block to change at least one of an incidence angle of the redirected scanned light into the procedure eye and the target location of the procedure eye. For example, the beam coupler 142 and/or the optical block 102 can be translated and/or rotated to change the incidence angle and/or target location of the scanned light beam 146 in the procedure eye 122.

In some embodiments, moving the beam coupler (step 260) can include rotating the beam coupler. For example, the beam coupler 142 can be rotated about at least of one of a first axis, a second axis, and a third axis (e.g., axes 132, 128 and 130). In some embodiments, moving the beam coupler (step 260) can include rotating the optical block about at least one of a first axis, a second axis, and a third axis (e.g., axes 128, 130, and 132) and/or translating the optical block along at least one of the first axis, the second axis, and the third axis (e.g., axes 128, 1302, 132). In some embodiments, the method 200 can include repeating the moving step to generate imaging information associated with different incidence angles and/or different target locations in the procedure eye and combining the imaging information associated to generate combined imaging information. For example, OCT data can be generated at various incidence angles and/or target locations. The OCT data from the individual angles and/or target locations can be combined or stitched together through one or more processing steps to generate OCT data for a wider field of view (e.g., a cross-sectional and/or volumetric scan). For example, a treatment beam can be delivered to various incidence angles and/or target locations.

Embodiments as described herein can provide devices, systems, and methods that facilitate real-time, intra-surgical, adjustable wide-angle beam scanning for diagnostic imaging and/or treatment beam delivery. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An ophthalmic surgical system comprising:
  at least one light source, configured to generate a light beam;
  a beam guidance system, configured to guide the light beam from the at least one light source;
  an optical block comprising:
    a beam scanner, configured to:
      receive the light from the beam guidance system, and
      generate a scanned light beam;
    a beam coupler, configured to redirect the scanned light beam, the beam scanner and the beam coupler are integrated into the optical block; and
  a wide field of view (WFOV) lens, configured to guide the redirected scanned light beam into a target region of a procedure eye;
  wherein:
  the optical block is movable with six degrees of freedom, a first degree of freedom being a rotation about an axis of the surgical microscope, a second degree of freedom being a rotation about an axis of the optical block; and
  the beam coupler is rotatable about an axis of the beam coupler, the beam coupler rotatable independent of movement of the optical block to change at least one of an incidence angle of the redirected scanned light beam into the procedure eye and the target region of the procedure eye.

2. The ophthalmic surgical system of claim 1, wherein:
  the at least one light source is configured to generate a diagnostic light beam.

3. The ophthalmic surgical system of claim 2, wherein:
  the at least one light source, the beam guidance system, and the beam scanner are part of an diagnostic imaging system; and
  the WFOV lens and the beam coupler are configured to guide a returned image light from the target region back to the diagnostic imaging system.

4. The ophthalmic surgical system of claim 3, wherein the diagnostic imaging system is at least one of:

an optical coherence tomography (OCT) system, a multispectral imaging system, a fluorescence imaging system, and a photo-acoustic imaging system.

5. The ophthalmic surgical system of claim 1, wherein: the at least one light source is configured to generate a treatment light beam.

6. The ophthalmic surgical system of claim 5, wherein: the at least one light source, the beam guidance system, and the beam scanner are part of a treatment beam delivery system.

7. The ophthalmic surgical system of claim 5, wherein the treatment beam delivery system is a laser beam delivery system.

8. The ophthalmic surgical system of claim 1, wherein: the at least one light source is configured to generate both a diagnostic light beam and a treatment light beam.

9. The ophthalmic surgical system of claim 1, wherein the beam scanner is configured to:
receive the diagnostic light beam from the beam guidance system;
generate a scanned diagnostic light beam;
receive the treatment light beam from the beam guidance system; and
generate a scanned treatment light beam.

10. The ophthalmic surgical system of claim 1, wherein: the beam coupler is configured to redirect the scanned light beam into an optical pathway of the surgical microscope; and
the beam coupler is positioned between the surgical microscope and the procedure eye, the beam coupler being movable relative to the surgical microscope and the procedure eye.

11. The ophthalmic surgical system of claim 10, wherein: the beam coupler comprises at least one of a dichroic mirror, a notch filter, a hot mirror, and a cold mirror in a tilted position.

12. The ophthalmic surgical system of claim 10, wherein: the beam coupler is coupled to the surgical microscope by at least one of a suspension system, a mechanical frame, a protruding arm, a conical structure, a magnetic member, an elastic member, and a plastic member.

13. The ophthalmic surgical system of claim 10, wherein: the beam coupler is operated without a defined optical/optomechanical relationship to the surgical microscope.

14. The ophthalmic surgical system of claim 13, wherein: the beam coupler is coupled to a support arm.

15. The ophthalmic surgical system of claim 1, wherein: the WFOV lens is a macular lens configured to be contacted to the procedure eye.

16. The ophthalmic surgical system of claim 1, wherein: the WFOV lens is an ocular lens configured to be spaced from the procedure eye.

17. The ophthalmic surgical system of claim 1, wherein: the beam scanner is at least one of a pair of scanning mirrors, a micro-mirror device, a MEMS based device, a deformable platform, a galvanometer-based scanner, a polygon scanner and a resonant PZT scanner.

18. The ophthalmic surgical system of claim 1, wherein: the beam guidance system comprises at least one of a fiber optical guide and a free space guidance system.

19. The ophthalmic surgical system of claim 1, wherein the optical block is a consumable product configured for use in a single surgical procedure.

* * * * *